United States Patent [19]

Seigneurin et al.

[11] Patent Number: 4,534,733
[45] Date of Patent: Aug. 13, 1985

[54] DEVICE FOR DENTAL MASSAGE TO PREVENT TOOTH DECAY

[75] Inventors: Michel Seigneurin, Douvaine; Roger Blanc, Chambery, both of France

[73] Assignee: Micro-Mega, Besancon, France

[21] Appl. No.: 554,359

[22] Filed: Nov. 22, 1983

[30] Foreign Application Priority Data

Apr. 6, 1983 [FR] France ................................ 83 05726

[51] Int. Cl.³ .............................................. A61C 3/03
[52] U.S. Cl. .................................... 433/122; 433/127; 433/147
[58] Field of Search ............... 433/118, 119, 122, 123, 433/124, 125, 126, 127, 165, 166, 115; 279/97; 74/49, 50

[56] References Cited

U.S. PATENT DOCUMENTS

| 1,711,846 | 5/1929 | Heilborn | 433/122 |
| 2,135,933 | 11/1938 | Blair | 433/166 |
| 3,407,503 | 10/1968 | Nealon | 433/76 |
| 4,460,341 | 7/1984 | Nakanishi | 433/122 |

FOREIGN PATENT DOCUMENTS

WO81/00113 4/1982 PCT Int'l. Appl. ................ 433/115

Primary Examiner—John J. Wilson
Attorney, Agent, or Firm—Robert E. Burns; Emmanuel J. Lobato; Bruce L. Adams

[57] ABSTRACT

A dental tool having a head with an output spindle to which are coupled dental treating devices such as a dental massaging brush. The output spindle is driven with a reciprocatory rotary motion imparted to it from a rotationally driven drive shaft coupled to the output spindle by a drive coupling device which converts the rotational motion of the drive shaft to reciprocatory rotary output of the output spindle. An O-ring effects a seal about the output spindle where it extends outwardly of the head. The drive coupling device has an eccentric stud fixed eccentrically to the drive shaft extending therefrom from one side to the other of a projection of the longitudinal axis of the drive shaft and making an angle with the projection of the axis. The eccentric stud is received in an axial slit in the output spindle for effecting the motion conversion.

5 Claims, 3 Drawing Figures

DEVICE FOR DENTAL MASSAGE TO PREVENT TOOTH DECAY

BACKGROUND OF THE INVENTION

The subject of the present invention is a device for the preventive treatment of dental decay by means of the mechanical action of massaging the enamel, of the type comprising a tool-holder provided with a head to which a massage cup or brush is connected, the said tool-holder incorporating on the inside means for driving the cup or brush in alternating rotation about its axis, the tool-holder incorporating on the inside means for converting a continuous rotational movement of the drive shaft into an alternating movement transmitted by the head of the tool-holder to the cup or to the brush.

Devices of this type are already known.

Thus, for example, U.S. Pat. No. 2,135,933 describes a device for driving in alternating rotation a cup for massaging the enamel. However, it is complex to produce and, above all, does not provide the necessary guarantee of leak-proofing for this type of use.

Many means of converting a continuous rotational movement into an alternating rotational movement are also known. French Pat. No. 1,455,922 in the Applicant's name is an example of this. In another technical field, but with a strictly identical function, Swiss Pat. No. 343,354 describes a device in which the axis of the drive stud is arranged inclined relative to the spindle to be driven.

These devices are of too fragile a structure for preventive treatment, and moreover they are not designed with sufficient leak-proofing for this use.

There is, therefore, a need for devices for preventive treatment which are both robust and leak-proof.

SUMMARY OF THE INVENTION

According to the invention, this result is achieved by means of a device for the preventive treatment of dental decay by the mechanical action of massaging the enamel, of the type comprising a tool-holder provided with a head to which a massage cup or brush is connected, the said tool-holder incorporating on the inside means for driving the cup or brush in alternating rotation about its axis, the tool-holder incorporating on the inside means for converting a continuous rotational movement into an alternating rotational movement transmitted by the head of the tool-holder to the cup or to the brush, characterised in that:

(a) the head spindle does not pass through the head body and it projects from the latter only on the same side as the cup or the brush which is fixed to it, (b) the head spindle is provided with an O-ring gasket, (c) the cups or brushes are fitted on a pin perpendicular to the head spindle and outside the head.

This guarantees substantially improved leak-proofing and much easier assembly and removal.

Advantageously, the drive is provided by a control stud mounted excentrically on a plate driven in continuous rotation by the drive shaft, the said control stud interacting with a slit passing through the head spindle and itself passing through the said spindle.

As a result of this drive, it will be understood that the device obtained is distinctly more robust in as much as, in diagrammatic terms, the stud pushes the head spindle and pulls it at one and the same time, the force being distributed over the entire length of the stud.

BRIEF DESCRIPTION OF THE DRAWINGS

The invention will be understood better by means of the following description made with reference to the attached drawings in which.

DESCRIPTION OF THE PREFERRED EMBODIMENTS

Figure 1:
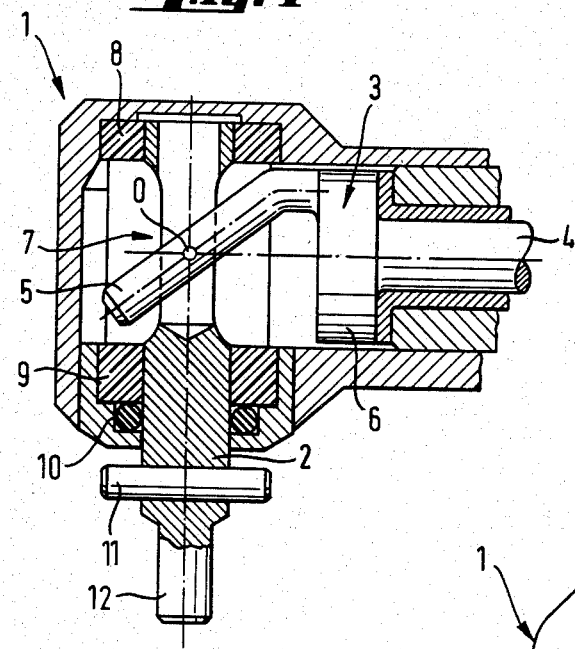
FIG. 1 is a sectional view of a preventive-treatment head according to the invention.

Reference will first be made to FIG. 1.

The preventive-treatment device according to the invention comprises essentially a leak-proof head (1), a head spindle (2) and a drive device (3).

The movement is transmitted from a rotary driven drive shaft (4) by means of a stud (5) mounted excentrically on a plate (6) fixed to the drive shaft.

The axis of the stud (5) is inclined approximately 45° relative to the axis of the drive shaft (4).

The stud (5) is arranged essentially within a slit (7) which passes completely or only partially through the head spindle (2) in its portion within the head (1).

The head spindle is mounted rotatably in the head (1) by means of the bearings (8, 9).

To ensure the best possible operation of the device, the axes of the drive shaft (4), the stud (5) and the head spindle (2) will converge at a point O.

In the upper part of the head (1), the problem of leak-proofing is solved by the simple fact that the head has no orifice or actuating means.

In the lower part, via which the head spindle projects, leak-proofing is ensured by means of an annular gasket (10). This solution may appear simple and obvious, but it is entirely original in substance and above all is effective in as much as it functions perfectly because the head spindle executes only quarter-turn rotations. Such leak-proofing on a spindle rotating continuously would be completely ineffectual.

To avoid complex structures for fastening the brushes or cups, which are also sources for the penetration of abrasive paste into the head, a specific attachment system has also been designed. For this purpose, a pin (11) is knocked in and secured to the head spindle (2) perpendicularly to the latter.

The spindle (2) terminates in its distal part in a spindle end of smaller diameter (12) which cooperates in fastening the brushes and cups, as will be explained later.

Figure 2:
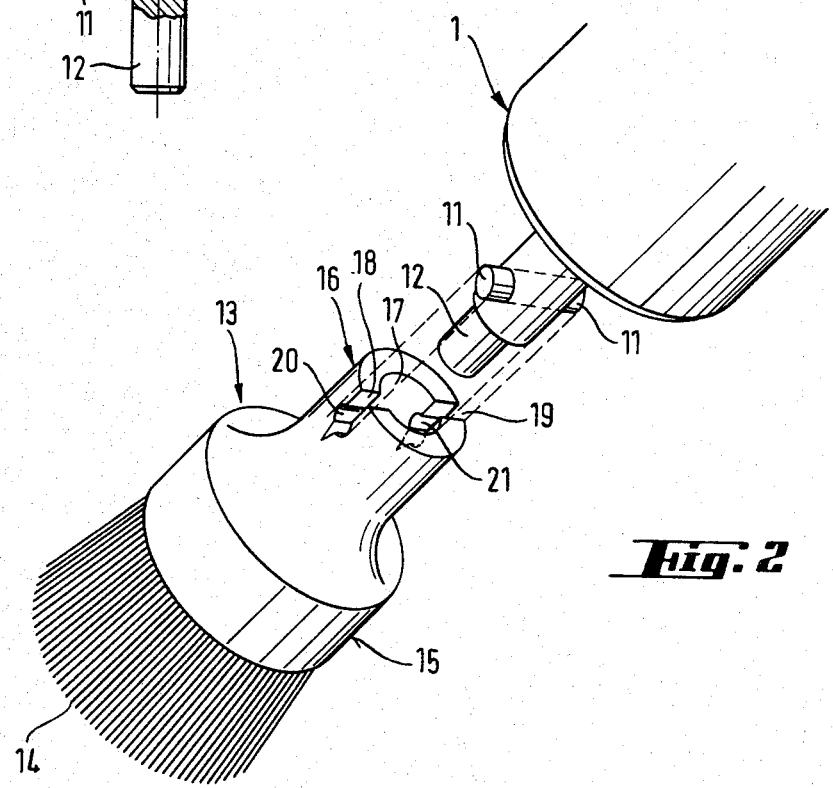
FIG. 2 is a profile view of a brush and its attachment device.

FIG. 2 shows a small removable brush (13) which can be fitted on the device of FIG. 1.

The brush (13) consists essentially of brushing bristles (14) planted in a body (15) having in its rear part an attachment device (16) comprising:

a central recess (17) intended for receiving the spindle end (12) of the head spindle, two slots (18, 19) provided with clearances (20, 21) in which the pin (11) is positioned.

The pin (11) is retained in the clearances (20, 21) because of the elasticity of the slits (18, 19) which resume their initial position after the passage of the pin (11), the diameter of which is greater than the width of the slits (18, 19).

In this way, it is possible to change the brushes without having to touch the head and in a very simple way, without the need for complex structures of the head which give rise to defective leak-proofing.

Figure 3:
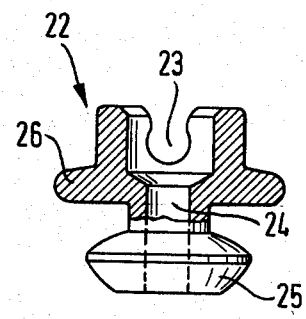
FIG. 3 is a sectional view of an adaptor for a cup intended to be used with the device according to the invention.

The brushes and cups can be designed specifically or mounted on adaptors of the type shown in FIG. 3.

The adaptor (22) comprises essentially a groove (23) intended for receiving the pin (11), a central recess (24) in which the spindle end (12) is accommodated, and a knob (25) intended for receiving the rubber cup. To prevent abrasive paste from flowing back up, the adaptor will incorporate a wing (26) keeping the paste down.

We claim:

1. In a dental tool, a head on the tool, a rotary drive shaft driven rotationally about its longitudinal axis, an output spindle driven reciprocably rotationally from the rotary drive shaft and having a part thereof extending out of said head with its axis of rotation normal to the longitudinal axis of the rotary drive shaft, bearings in said head mounting the output spindle for reciprocatory rotation, a drive device coupling the rotary drive shaft and the output spindle and converting the rotary motion of the drive shaft to reciprocatory rotary motion of the output spindle comprising an eccentric stud mounted eccentrically on the drive shaft extending therefrom at an angle relative to a projection of the longitudinal axis of the drive shaft, the output spindle having an axial slit into which the eccentric stud extends, the stud having a point of connection to the rotary shaft eccentric to the longitudinal axis and extending therefrom to another point on another side of said longitudinal axis and eccentric thereto, the output spindle having surfaces coactive with the stud for driving the stud with said reciprocatory rotary motion when the drive shaft is driven rotationally.

2. In a dental tool according to claim 1, including a coupling projection extending laterally from said output spindle.

3. In a dental tool according to claim 2, including a massaging brush having an opening into which said output spindle extends, and a recess in which said coupling projection is received for removably mounting the massaging brush on the output spindle.

4. In a dental tool according to claim 1, in which said head has a casing and including an O-ring effecting a tight seal between the head and said part of the output spindle where it extends out of the head, said O-ring being mounted between the casing and one of said bearings.

5. In a dental tool according to claim 1, including an adapter removably mounted on the tool for driving by the output spindle having an axial opening into which the output spindle extends and a transverse recess for receiving said coupling projection, the adapter having a knob at an end thereof for mounting a treatment device thereon, a circumferential flange adjacent the knob for precluding treatment paste applied from flowing toward the tool head.

* * * * *